US011008363B2

(12) United States Patent
Prasad et al.

(10) Patent No.: US 11,008,363 B2
(45) Date of Patent: *May 18, 2021

(54) PREPARATION OF BILE ACIDS AND INTERMEDIATES THEREOF

(71) Applicant: ALLERGAN SALES, LLC, Madison, NJ (US)

(72) Inventors: Achampeta Rathan Prasad, Hyderabad (IN); Roy A. Swaringen, Jr., Durham, NC (US); John Gregory Reid, Groton, MA (US); Robert M. Moriarty, Michiana Shores, IN (US); Akhila Kumar Sahoo, Hyderabad (IN)

(73) Assignee: Allergan Sales, LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/856,374

(22) Filed: Apr. 23, 2020

(65) Prior Publication Data

US 2020/0317716 A1  Oct. 8, 2020

Related U.S. Application Data

(60) Continuation of application No. 16/051,409, filed on Jul. 31, 2018, now Pat. No. 10,633,412, which is a division of application No. 14/696,204, filed on Apr. 24, 2015, now Pat. No. 10,053,486, which is a division of application No. 13/752,175, filed on Jan. 28, 2013, now abandoned, which is a continuation of application No. 13/010,727, filed on Jan. 20, 2011, now Pat. No. 8,362,285, which is a division of application No. 12/613,969, filed on Nov. 6, 2009, now Pat. No. 7,994,351, which is a continuation of application No. 12/153,446, filed on May 16, 2008, now Pat. No. 7,902,387.

(30) Foreign Application Priority Data

Apr. 25, 2008 (GB) ..................................... 0807615

(51) Int. Cl.
| | |
|---|---|
| *C07J 9/00* | (2006.01) |
| *C07J 75/00* | (2006.01) |
| *C07J 1/00* | (2006.01) |
| *C07J 13/00* | (2006.01) |

(52) U.S. Cl.
CPC ................ *C07J 9/005* (2013.01); *C07J 1/00* (2013.01); *C07J 1/0011* (2013.01); *C07J 9/00* (2013.01); *C07J 13/00* (2013.01); *C07J 13/007* (2013.01); *C07J 75/00* (2013.01)

(58) Field of Classification Search
CPC .............. C07J 9/00; C07J 9/005; C07J 75/00
See application file for complete search history.

(56) References Cited

U.S. PATENT DOCUMENTS

| | | | |
|---|---|---|---|
| 2,321,598 | A | 6/1943 | Hoehn et al. |
| 2,509,248 | A | 5/1950 | Hastings Sarett et al. |
| 2,615,902 | A | 10/1952 | Hirschmann et al. |
| 2,765,316 | A | 2/1956 | Sifferd et al. |
| 3,065,227 | A | 11/1962 | Dodson |
| 3,836,516 | A | 9/1974 | Stempel et al. |
| 3,891,677 | A | 6/1975 | Tanabe |
| 4,113,882 | A | 9/1978 | Okazaki et al. |
| 4,226,770 | A | 10/1980 | Kaiser |
| 4,310,467 | A | 1/1982 | Batcho et al. |
| 4,322,553 | A | 3/1982 | Chupp |
| 4,594,432 | A | 6/1986 | Baggiolini et al. |
| 4,681,876 | A | 7/1987 | Marples et al. |
| 4,762,919 | A | 8/1988 | Lee |
| 4,866,044 | A | 9/1989 | Sato et al. |
| 4,917,827 | A | 4/1990 | Batist et al. |
| 5,194,602 | A | 3/1993 | Batisi et al. |
| 5,304,551 | A | 4/1994 | Marples et al. |
| 5,827,853 | A | 10/1998 | Blanc-Ferras et al. |
| 6,114,336 | A | 9/2000 | Blanc-Ferras et al. |
| 6,136,851 | A | 10/2000 | Bonte et al. |
| 6,313,128 | B1 | 11/2001 | Blanc-Ferras et al. |
| 6,417,179 | B1 | 7/2002 | Burkhart et al. |
| 6,572,399 | B2 | 6/2003 | Shimirak |
| 6,573,299 | B1 | 6/2003 | Petrus |
| 6,610,866 | B2 | 8/2003 | Kinney et al. |
| 6,653,492 | B2 | 11/2003 | Faarup |
| 6,936,402 | B2 | 8/2005 | Kim et al. |
| 7,052,716 | B1 | 5/2006 | Lanzendorfer et al. |
| 7,166,299 | B2 | 1/2007 | Yoo |
| 7,601,706 | B2 | 10/2009 | Cundy et al. |
| 7,622,130 | B2 | 11/2009 | Kolodney et al. |
| 7,754,230 | B2 | 7/2010 | Kolodney et al. |
| 7,902,387 | B2 | 3/2011 | Prasad et al. |
| 8,242,294 | B2 | 8/2012 | Moriarty et al. |
| 8,298,556 | B2 | 10/2012 | Kolodney et al. |
| 8,461,140 | B2 | 6/2013 | Moriarty et al. |

(Continued)

FOREIGN PATENT DOCUMENTS

| | | |
|---|---|---|
| CL | 44393 | 9/2000 |
| CN | 1180519 A | 5/1998 |

(Continued)

OTHER PUBLICATIONS

US 4,595,432 A, 06/1986, Baggiolini et al. (withdrawn)
U.S. Appl. No. 13/490,137, filed Jun. 6, 2012, Moriarty et al.
U.S. Appl. No. 14/732,515, filed Jun. 5, 2015, Moriarty et al.
"Deoxycholic Acid". New Zealand Pharamceuticals Ltd., (2007) http://www.nzp.co.nz/products.php?cid=2&pid=2.
Arnone et al., "Perfluoro-cis-2,3-Dialkyloxaziridines: Effective Reagents for the Selective Oxidation of Ethers to Carbonyl Compounds." Journal of Organic Chemistry, 1995, vol. 60(8), pp. 2314-2315.
Avissar et al., "Plasma Selenium-dependent Glutathione Peroxidase," J. Biol. Chem., (1989), 264(27):15850-15855.

(Continued)

*Primary Examiner* — Barbara P Badio
(74) *Attorney, Agent, or Firm* — Foley & Lardner LLP

(57) ABSTRACT

Synthetic methods for preparing deoxycholic acid and intermediates thereof are provided.

10 Claims, 1 Drawing Sheet

(56) References Cited

U.S. PATENT DOCUMENTS

| | | | |
|---|---|---|---|
| 8,546,367 B2 | 10/2013 | Moriarty et al. |
| 8,653,058 B2 | 2/2014 | Hodge et al. |
| 8,883,770 B2 | 11/2014 | Moriarty et al. |
| 9,050,349 B2 | 6/2015 | Moriarty et al. |
| 9,636,349 B2 | 5/2017 | Moriarty et al. |
| 9,987,291 B2 | 6/2018 | Moriarty et al. |
| 2002/0037977 A1 | 3/2002 | Feldstein et al. |
| 2004/0118412 A1 | 6/2004 | Piletti-Reyes |
| 2005/0042539 A1 | 2/2005 | Kim et al. |
| 2005/0089555 A1 | 4/2005 | Boderke et al. |
| 2005/0261258 A1 | 11/2005 | Kolodney et al. |
| 2005/0267080 A1 | 12/2005 | Kolodney et al. |
| 2006/0127468 A1 | 6/2006 | Kolodney et al. |
| 2006/0154906 A1 | 7/2006 | Kolodney et al. |
| 2006/0222695 A1 | 10/2006 | Zadini et al. |
| 2007/0032464 A1 | 2/2007 | Liao et al. |
| 2008/0004446 A1 | 1/2008 | Pandey et al. |
| 2008/0114012 A1 | 5/2008 | Ohmoto et al. |
| 2008/0318870 A1 | 12/2008 | Moriarty et al. |
| 2008/0319221 A1 | 12/2008 | Junker et al. |
| 2009/0270642 A1 | 10/2009 | Prasad et al. |
| 2010/0060276 A1 | 3/2010 | Zur |
| 2010/0130426 A1 | 5/2010 | Young et al. |
| 2010/0145083 A1 | 6/2010 | Prasad et al. |
| 2010/0160276 A1 | 6/2010 | Moriarty et al. |
| 2011/0152552 A1 | 6/2011 | Prasad et al. |
| 2011/0224448 A1 | 9/2011 | Prasad et al. |
| 2013/0029958 A1 | 1/2013 | Moriarty et al. |
| 2013/0190517 A1 | 7/2013 | Prasad et al. |
| 2013/0252931 A1 | 9/2013 | Moriarty et al. |
| 2013/0267721 A1 | 10/2013 | Prasad et al. |
| 2015/0051182 A1 | 2/2015 | Kolodney et al. |
| 2015/0094261 A1 | 4/2015 | Moriarty et al. |
| 2016/0022700 A1 | 1/2016 | Moriarty et al. |
| 2018/0221391 A1 | 8/2018 | Moriarty et al. |
| 2018/0338987 A1 | 11/2018 | Moriarty et al. |

FOREIGN PATENT DOCUMENTS

| | | |
|---|---|---|
| CN | 1358193 | 7/2002 |
| EP | 0 336 521 A1 | 10/1989 |
| EP | 1 980 248 | 10/2008 |
| FR | 2858413 A1 | 2/2005 |
| GB | 1 214 093 A | 12/1970 |
| TW | 324062 | 5/2010 |
| WO | WO-93/03732 A1 | 3/1993 |
| WO | WO-94/27608 A1 | 12/1994 |
| WO | WO-98/05337 A1 | 2/1998 |
| WO | WO-01/70151 A1 | 9/2001 |
| WO | WO-02/088166 A1 | 11/2002 |
| WO | WO-2005/112942 | 12/2005 |
| WO | WO-2005/117900 A1 | 12/2005 |
| WO | WO-2006/086038 A1 | 8/2006 |
| WO | WO-2006/133160 A2 | 12/2006 |
| WO | WO-2008/157635 A2 | 12/2008 |

OTHER PUBLICATIONS

Babcock, et al., "Reduction Methylation of Steroid Ketones", J. Am. Chem. Soc., Nov. 5, 1952, vol. 74, pp. 5472-5474.

Barton et al. "A practical catalytic method for the preparation of steroidal 1,4-dien-3-ones by oxygen atom transfer from iodoxybenzene to diphenyl diselenide", J. Chem. Soc., Perkin Transactions 1: Organic and Bio-Organic Chemistry (1972-1999) (1982), (8), 1947-1952.

Batcho et al. "C-20 Stereospecific Introduction of a Steroid Side Chain." Journal of the American Chemical Society, 1981, vol. 103(5), pp. 1293-1295.

Bell, et al., "Microbiological hydroxylation. Part XVIII. Introduction of 16-, 9-, and 3-hydroxy-groups into dioxygenated 5-androstanes by the fungus *Diaporthe celastrina*", J. Chem. Soc., Perkin Transactions 1: Organic and Bio-Organic Chemistry (1972-1999) (1975), (14), 1364-1366.

Bril et al., "Fractionation of spinach chloroplasts with sodium deoxycholate," Biochim. Biophys. Acta, (1969), 172:345-348.

Caspi, E. "Degradation of corticosteroids. III.1,2 Catalytic Hydrogenation of Cortisol", J. Org. Chem., 1959, 24, 669-673.

Chambers, V.E.M. et al., "Microbiological Hydroxylation. Part XIV.1 Hydroxylation in the Terminal Rings of Dioxygenated 5a-Androstanes with the Fungi *Wojnowicia graminis* and *Ophiobolus herpotrichus*", J.C.S. Perkin I, Jun. 27, 1974, Apr. 1285, pp. 55-58.

Chang et al. "Seroflocculating Steroids" Clin. Chem. (1964), 10(1), 83-91.

Chang et al. "Seroflocculating Steroids. II. General." Contribution from the Division of Chemistry and Division of Pathology and Microbiology, Medical Units, University of Tennessee. (1957) 79:2161-2163.

Chen et al., "Formation of Sodium Dodecyl Sulfate-stable Fibronectin Multimers," J Biol. Chem., (1996), 271 (15):9084-9089.

Child et al., "Preparation and mass spectral behavior of some 5β-cholenoic acids." Canadian Journal of Biochemistry, 1979, vol. 57(3), pp. 216-225.

Cho et al., "α-Lipoic Acid Inhibits Adipocyte Differentiation by Regulating Pro-adipogenic Transcription Factors via Mitogen-activated Protein Kinase Pathways," J. Biol. Chem, 2003, 278(37):34823-34833.

Complaint for Patent Infringement, *Kythera Biopharmaceuticals, Inc. v. Slayback Pharma LLC*, Filed Nov. 9, 2018.

Crowley et al., "□□ The NAD+ precursors, nicotinic acid and nicotinamide protect cells against apoptosis induced by a multiple stress inducer, deoxycholate," Cell Death and Differentiation, (2000), 7:314-326.

Danielsson et al. "On the Composition of the Bile Acid Fraction of Rabbit Feces and the Isolation of a New Bile Acid: 3a, 12a-Dihydroxy-5a-cholanic Acid". The Journal of Biological Chemistry, (1963) 238 (12): 3846-3852.

Dawson, "The Biochemist's Handbook," MIR publishers, 1991, p. 173.

Dias et al., "13C nuclear magnetic resonance data of bile acid derivatives." Spectrochimica Acta, Part A: Molecular and Biomolecular Spectroscopy, 2000, vol. 56A(1), pp. 53-77.

Dobriner, K., et al. "The Isolation of ?9-Etiocholenol-3(a)-One-17 From Human Urine", Journal of Biological Chemistry (1947), 169, 221-222.

Dodson et al. "Microbiological Transformations. VII. The Hydroxylation of Steroids at C-9". Contribution from the Biological and Chemical Search Divisions of G. D. Searle and Co., Chicago 80, ILL., (1961) vol. 83: 4631-4635.

Duncan et al., "Lipodissolve for Subcutaneous Fat Reduction and Skin Retraction," Aesthetic Surgery Journal, (2005), 25(5):530-543.

FDA Guidance for Industry, Q6B Specifications: Test Procedures and Acceptance Criteria for Biotechnological/Biological Products, U.S. Department of Health and Human Services Food and Drug Administration, Aug. 1999.

Fieser et al., "Oxidation of Steroids. III. Selective Oxidations and Acylations in the Bile Acid Series", J. Am. Chem. Society, (1950), 72(12):5530-5536 XP055061601.

Fieser, L.F. et al., "Oxidation of Steroids. IV. Methyl ?9(11)-Litnocnoienate and Methyl 9a,11a-Oxidolithocholanate1,2", Jan. 1951, vol. 73, pp. 118-122.

Fukushima, D. et al. "The Characterization of Four New Metabolites of Adrenocortical Hormones", Journal of Biological Chemistry (1955), 212, 449-460.

Gallo-Torres et al., "Some effects of deoxycholate administration on the metabolism of cholesterol in man." The American Journal of Clinical Nutrition, vol. 32, pp. 1363-1375, 1979.

Gething et al., "Purification of fusion protein of Sendai virus: Analysis of the NH2-terminal sequence generated during precursor activation," Proc. Natl. Acad. Sci., (1978), 75(6):2737-2740.

Herzog, et al., "11-Oxygenated steroids. II. The reduction of 11-carbonyl to 11-alpha-hydroxyl in the etiocholane series," J. Am. Chem. Soc., (1953), 75(2):269-272 (XP002509785).

Heymann, H. et al., "A New Route to 11-Ketosteroids by Fission of a 9(11)-Ethylene Oxide", J. Am. Chem. Soc., Nov. 1951, vol. 73, pp. 5252-5265.

(56) References Cited

OTHER PUBLICATIONS

Hofmann et al. "A proposed nomenclature for bile acids". J. Lipid Res. (1992) 33: 599-604.

Hofmann et al., "Physicochemical properties of bile acids and their relationship to biological properties: an overview of the problem," J. Lipid Res., (1984), 25:1477-1489.

Hofmann, et al., "Bile acid solubility and precipitation in vitro and in vivo: the role of conjugation, pH, and Ca2 ions," J Lipid Res., (1992), 33:617-626.

Hofmann. "Bile Acids: The good, the Bad, and the Ugly". News Physiol. Sci. (1999) 14: 24-29.

Iida, T. et al., "A facile one-step synthesis of Delta 1-4-3-keto bile acid esters by iodoxybenzene and benzeneselenic anhydride," Journal of Lipid Research, 29(8), 1988, 1097-1101.

Iuliano et al., "Synthesis of deoxycholic-derived chiral stationary phases possessing both arylcarbamate and arylamide moieties: evaluation of their chiral discrimination properties in the HPLC resolution of racemic compounds." Tetrahedron: Asymmetry, 2001, vol. 12(20), pp. 2811-2825.

Jones, R.N., et al. "Studies in Steroid Metabolism. IV. The Characterization of Carbonyl and Other Functional Groups in Steroids by Infrared Spectrometry", J. Am. Chem. Soc. (1948), 70, 2024-2034.

Kagan et al. "No. 118.—Preparation Et Proprieties De Quelques Dioxolanes Derives D'Acides Biliaires" Bulletin de la Societe Chimique de France (1957), 699-704.

Kakushima, "Total synthesis of (±)-5β,8a-androst-9(11)-ene-3,17-dione," Canadian Journal of Chemistry, 1979, vol. 57(24), pp. 3354-3356.

Kametani et al. "First Total Synthesis of (+)-Chenodeoxycholic Acid". J. Am. Chem. Soc.. (1981) 103: 2890-2891.

Kandrac, J. et al, "Isolation and Determination of Bile Acids," Eur. J. Drug metabolism and Pharmacokinetics., (2006), 31(3), 157-177.

Kasal, "Hydrogenation of 12-Oxo-5β-Chol-9(11)-Enates on Platinum" Collection of Czechoslovak Chemical Communications (1981), 46(8), 1839-49.

Katona et al. "Synthesis, Characterization, and Receptor Interaction Profiles of Enantiomeric Bile Acids". J. Med. Chem., (2007) 50, 6048-6058.

Katona, et al. "Enantiomeric Deoxycholic Acid: Total Synthesis, Characterization, and Preliminary Toxicity toward Colon Cancer Cell Lines". J. Org. Chem., (2007) 72, 9298-9307.

Kiprianov, G. I.; Volovel'skii, L. N. Zhurnal Obshchei Khimii (1964), 34(1), 336-8.

Kondo et al., "Studies on the transformation of steroids by microorganisms—XI", Tetrahedron (1967), 23(5):2153-2158.

Kuhajda et al., "One-pot esterification and selective 3.alpha.-acetylation of cholic and deoxycholic acid," Collection of Czechoslovak Chemical Communications, (1996), 61(7):1073-1076 XP009169337.

Kyd, P., et al. "Experimental oleic acid-induced cholelithiasis in the rabbit associated with increased biliary 5-deoxycholic acid", Biochemical Journal (1972), 128(1), 169-172.

Li et al., "Gareth Rowlands" Jan. 1, 2002, pp. 45-58, XP055344949, Retrieved from the Internet: URL:http://www.massey.ac.nz/~gjrowlan/oxid/meta.pdf [retrieved on Feb. 13, 2017].

Lichtenberg et al., "On the solubility of calcium deoxycholate: kinetics of precipitation and the effect of conjugated bile salts and lecithin," Chem. Phys. Lipids, (1988), 46:279-291.

Lieberman, et al., "Studies in steroid metabolism," J. Biol. Chem., (1952), 196 (2):793-805, XP002509784.

Lieberman, S. et al., "Studies in Steroid Metabolism II. Identification and Characterization of Ketosteroids Isolated from Urine of Healthy and Diseased Persons," The Journal of Biological Chemistry 1948, 172, 263-295.

Lodish, et al. "Section 3.5—Purifying, Detecting and Characterizing Proteins," Molecular Cell Biology. 4th edition. New York: W. H. Freeman; 2000 pp. 83-99.

Luche et al., "Lanthanides in organic chemistry, 1. Selective 1,2 reductions of conjugated ketones", Journal of the American Chemical Society, American Chemical Society, (1978), vol. 100(7): 2226-2227, XP003010366, ISSN: 0002-7863, DOI: 10.1021/JA00475A040.

MacLachlan I., "Liposomal Formulations for Nucleic Acid Delivery," In Antisense Drug Technology, Principles, Strategies and Applications, 2nd Edition, Crooke S.T.; Ed.; Taylor & Francis Group, (2007), 237-270 ("MacLachlin 2007") at 253.

Mahler et al.,"Protein Aggregation: Pathways, Induction Factors, and Analysis," J. Pharm. Sci., (2009), 98(9):2909-2934.

Maneerat et al. "Bile acids are new products of a marine bacterium, *Myroides* sp. Strain SM1". Appl. Microbiol. Biotechnol., (2005) 67: 679-683.

Marker et al. "Sterols. LXIX. Oxidation Products of Sarsasapogenin. Sarsasapogenoic Acid and Related Substances". J. Am. Chem. Soc., (1939) 61(8): p. 2072-2077.

Martins et al., "Lipid-based colloidal carriers for peptide and protein delivery—liposomes versus lipid nanoparticles," Int. J Nanomedicine, (2007), 2(4):595-607.

Matsuoka et al. "Micelle formation of sodium deoxycholate and sodium ursodeoxycholate (Part 1)". Biochem. Biophys. Acta. 1580, (2002) pp. 189-199.

Mazur et al. "The Synthesis of the Steroidal Sepogenins". J. Am. Chem. Soc., (1960) 82, 5889-5908.

McKenzie et al., "Steroids Derived From Bile Acids," from the Division of Biochemistry, May Foundation, Rochester, Minnesota, (1948) (069611-0699).

Micheli, et al. "Total Syntheses of Optically Active 19-Norsteroids. (+)-Estr-4-ene-3,17-dione and (+)-13β-Ethylgon-4-ene-3,17-dione". J. Org. Chem., (1975) vol. 40, No. 6, pp. 675-681.

Mickova et al., "Reduction of 12-oxo derivatives of some bile acids," Collection of Czechoslovak Chemical Communications, (1985), 50(5):1239-1243 XP009169299.

Mukawa, K. et al., "Studies on the Transformation of Unnatural Steroids by Micro-organisms. 14-βHydroxylation of Androstane Derivative," Journal of the Chemical Society: Chemical Communications, 1971, vol. 18, pp. 1060-1061.

Mukhopadhyay et al., "Chemistry and biology of bile acids." Current Science, (2004) 87(12)1666-1683.

Murata et al., "Study of the Micelle Formation of Sodium Deoxycholate. Concentration Dependence of Carbon-13 Nuclear Magnetic Resonance Chemical Shift," J. Phys. Chem., (1982), 86:4690-4694.

Murata et al., "Study on the Micelle Formation of Sodium Deoxycholate, in Solution Behavior of Surfactants," Eds., Mittal K.L. et al., Plenum Press, New York, (1982), 611-627.

Narain, et al., "Lecithin Protects against Plasma Membrane Disruption by Bile Salts," J. Surg. Res., (1998), 78(2):131-136.

Okuda, et al., "The Organic Composition of Earwax," J. Otolaryngol., (1991), 20(3):212-215.

Osawa "Dehydration of Bile Acids and Their Derivatives. X. A Study of the Physical Properties of Various 3a-Hydroxycholenates and Their Derivatives, With Special Reference to Their Optical Rotatory Dispersions" Bulletin of the Chemical Society of Japan (1962), 35(3), 381-7.

Peron et al. "Steroids of Guinea Pig Urine," Journal of Biological Chemistry (1956), 223, 877-883.

Petrow et al., "Steroids and Related Compounds. Part II. The Dehydration of Cholestanetriol," J. Chem. Soc., (1938), 677-681.

Potluri, V.K. et al., "Bile Acid-Derived Molecular Tweezers: Study of Solvent Effects in Binding, and Determination of Thermodynamic Parameters by an Extraction-Based Protocol," J. Org. Chem., 2000, 65, 7764-7769.

Quan Hua, "Review of Tropospheric Bomb 14C Data for Carbon Cycle Modeling and Age Calibration Purpose," Radiocarbon, (2004), 46(3):1273-1298.

Rao et al., "Synthesis of a precursor for the preparation of 9α, 11α-tritiated 5α-androstane-3α, 17β-diol 17-glucuronide," Steroids, (1984), 43(3):343-350.

Reichstein et al. "Über Gallensäuren und verwandte Stoffe. 12. Mitteilung. Vereinfachte präparative Herstellung reiner Desoxycholsäure und eigener ihrer Derivate" Helvetica Chimica Acta, vol. 25, No. 5, Oct. 24, 2004 (Oct. 24, 2004), pp. 797-805, XP002509789.

Ridlon et al. "Bile salt biotransformations by human intestinal bacteria". J. Lipid Res., (2006) 47(2): p. 241-259.

(56) References Cited

OTHER PUBLICATIONS

Rittes, P. G., "The Use of Phosphatidylcholine for Correction of Localized Fat Deposits," Aesth. Plast. Surg. (2003), 27:315-318.
Rittes, P. G., "The use of Phosphatidylcholine for Correction of Lower Lid Bulging Due to Prominent Fat Pads," Dermatol. Surg., (2001), vol. 27:4, pp. 391-392.
Roda et al. "Quantitative aspects of the interaction of bile acids with human serum albumin". J. Lipid Res. (1982) 23(3): p. 490-495.
Rotunda et al. "Lipomas treated with subcutaneous deoxycholate injections." J. Am. Acad. Dermatol., (2005) pp. 973-978.
Rotunda et al. "Mesotherapy and Phosphatidylcholine Injections: Historical Clarification and Review" Dermatologic Surgery, (2006) 32: 465-480.
Rotunda, et al., "Detergent effects of sodium deoxycholate are a major feature of an injectable phosphatidylcholine formulation used for localized fat dissolution," Dermatol. Surg., (2004), 30(7):1001-1008.
Ryden et al., "The effects of pH and bile salts on the binding of MelQx to wheat bran fibre," Mutation Res., (1996), 351:45-52.
Sachs et al., "The Effect of Pyrophosphate on the Amino Acid Incorporating System of Rat Liver Microsomes," J. Biol. Chem., (1958), 233(3):650-656.
Sarett, L.H. et al., "Partial Synthesis of Etiocholene-9-Ol-3(a)-One-17", The Journal of Biological Chemistry, ASBMB, www.jbc.org, Dec. 5, 1947, pp. 185-187.
Schow et al., "Utility of the Wittig Reaction for the Construction of Side Chains of Steroids Starting from Pregnenolone," J. Org. Chem., (1979), vol. 44(22):3760-3765.
Scott et al. "A Symmetry Rule for Chiral Olefins" Tetrahedron (1970), 26(15), 3695-3715.
Shirasaka, M., et al. "The microbial reduction of [Delta]4-3-ketone pregnene compounds by a fungus, *Alternaria bataticola*", Biochemistry and Biophysics (1959), 85, 277-280.
Shopee et al., "96. Androsten-(9)-dion-(3,17), Bemerkungen zu H.Reich und A. Lardon1), Androsten-(9)-ol-(3β)-on-(17)," vol. xxx, Fasciculus III (1947), pp. 766-768.
Shoppee. "252. The Structure of Adreno-cortical Metabolites: ?9:11-Androstene-3 : 17-dione." J. Chem. Soc., 1946, 1134-1137.
Sigma Product Information Sheet, RIP A Buffer, Product No. R0278, Sep. 2003.
Sigma Product Information Sheet, Sodium deoxycholate,Product No. D6750, May 2006.
Small, "Size and Structure of Bile Salt Micelles. Influence of Structure, Concentration, Counterion Concentration, pH, and Temperature", in Molecular Association in Biological and Related Systems; Goddard, E.; Advances in Chemistry; American Chemical Society: Washington, DC, 31-52, 1968.
Smith, S. , "A Heated Debate on Hot Shot Fat-Zapper," The New York Post, Dec. 8, 2002, 12.
Snider, Barry B., "Lewis-Acid-Catalyzed Ene Reactions," Acc. Chem. Res., (1980), 13:426-432.
Stavroudis C., "Sorting Out Surfactants," WAAC Newsletter, (2009), 31(1):18-21.
Stefanovic, M., et al. "An improved preparation of 3-[alpha]-acetoxy-11,20-diketo-(5[beta])-pregnane, the key intermediate in the synthesis of 11-oxygenated corticosteroids", Tetrahedron Letters (1967), (48), 4799-4803.
Stoll et al., "In Vitro Dissolution and In Vivo Absorption of Nitrofurantoin from Deoxycholic Acid Coprecipitates," J Pharm. Sci., (1973), 62(1):65-68.
Su et al., "Regulation of System A Amino Acid Transport in 3T3-L1 Adipocytes by Insulin." J. Biol. Chem., (1998), 273(6):3173-3179.
Svensson et al. "The Design and Bioactivation of Presystemically Stable Prodrugs". Drug Metabolism Reviews, (1988) 19(2): 165-194.
Szczebara et al. "Total biosynthesis of hydrocortisone from a simple carbon source in yeast". Nature Publishing Group, (2003) vol. 21:143-149.
Szczepanik et al., "Characterization of bile acid methyl ester acetate derivatives using gas-liquid chromatography, electron impact, and chemical ionization mass spectrometry." Journal of Lipid Research, 1976, vol. 17(4), pp. 314-334.
Talmage et al. "Quingestrone—Determination of Minute Quantities of Decomposition Products by Paper Chromatography" Journal of Pharmaceutical Sciences (1964), 53(1), 76-9.
Tsuji et al., "Highly Stereoselective Hydrogenation of 3-Oxo-4-ene and -1,4-diene Steroids to 5-beta Compounds with Palladium Catalyst" J. Org. Chem., (1980), 45(13):2729-2731.
Wendel, A., Lecitnin: The First 150 Years—Part II: evolution to a global pnarmaceutical industry, Inform, (2000), 11:992-997.
Woodward et. al. "The Total Synthesis of Steroids". J. Am. Chem. Soc., (1952) 74(17) : 4223-4251.
Wright et al., "Formulation Development of AAV2 Vectors: Identification of Excipients That Inhibit Vector Aggregation," Mo. Therapy, (2004), 9(Supplement 1):S163, Abstract 425.
Yoshizawa et al., "Isolation and Structural Elucidation of the Degradation Products of Pregnanediol Disulfate obtained by Hot Acid Hydrolysis (Clinical Analysis on Steroids. XXII))." Chemical & Pharmaceutical Bulletin, 1982, vol. 30(7), pp. 2474-2486.
Zhang et al., "A potent small molecule inhibits polyglutamine aggregation in Huntington's disease neurons and suppresses neurodegeneration in vivo," Proc. Natl. Acad. Sci., (2005), 102(3):892-897.
Ziegler et al., "The AlCl3—LiAlH4 reduction of 9(11)-12-oxo and ?9(11)-12-hydroxy steroids." Canadian Journal of Chemistry, 1968, vol. 46(9), pp. 1574-1577.

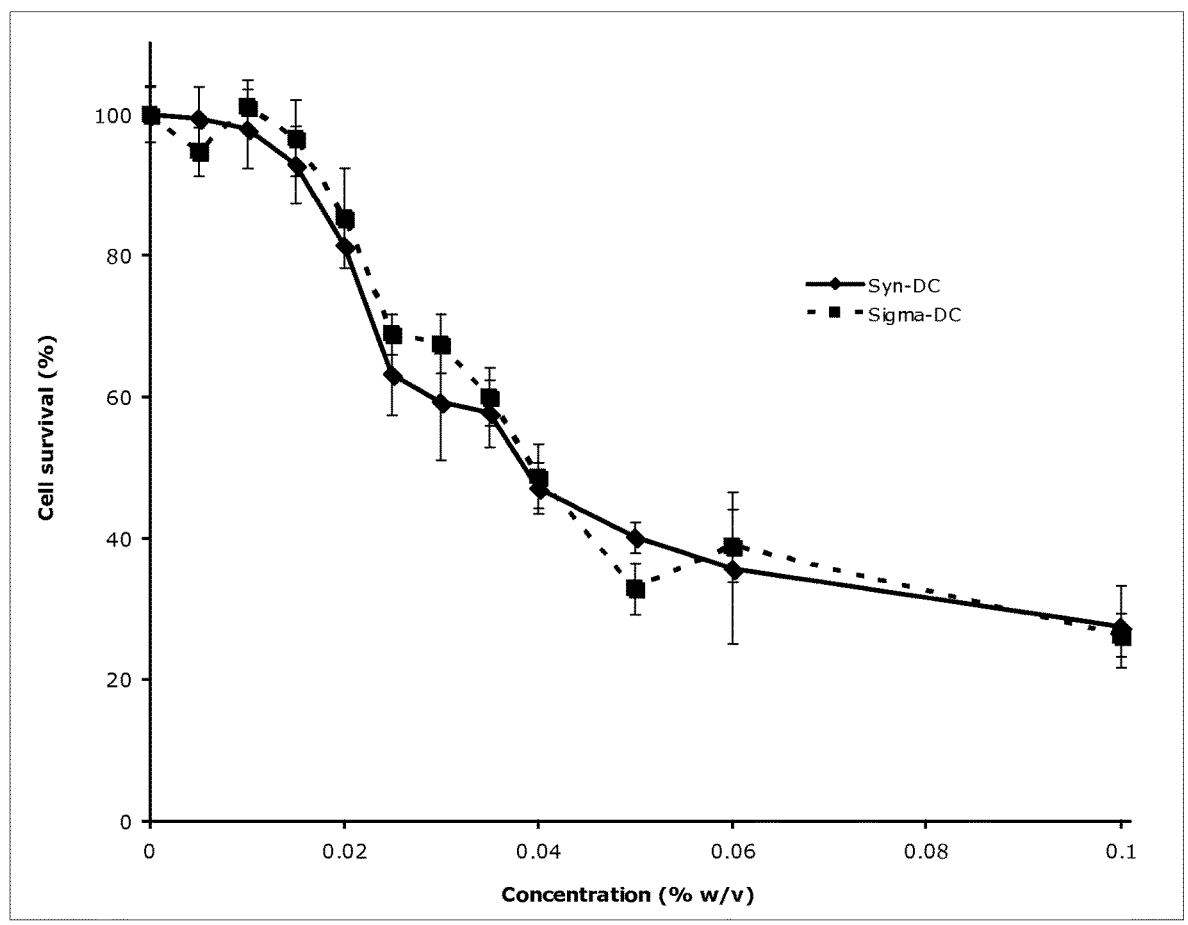

PREPARATION OF BILE ACIDS AND INTERMEDIATES THEREOF

CROSS REFERENCE TO RELATED APPLICATION

This application is a continuation of U.S. patent application Ser. No. 16/051,409, filed Jul. 31, 2018, pending, which is a divisional of U.S. patent application Ser. No. 14/696,204, filed Apr. 24, 2015, issued as U.S. Pat. No. 10,053,486 on Aug. 21, 2018, which is a divisional of U.S. patent application Ser. No. 13/752,175, filed Jan. 28, 2013; now abandoned, which is a continuation of U.S. patent application Ser. No. 13/010,727, filed Jan. 20, 2011, issued as U.S. Pat. No. 8,362,285; which is a divisional of U.S. patent application Ser. No. 12/613,969, filed Nov. 6, 2009, issued as U.S. Pat. No. 7,994,351 on Aug. 9, 2011; which is a continuation of U.S. patent application Ser. No. 12/153,446, filed May 16, 2008, issued as U.S. Pat. No. 7,902,387 on Mar. 8, 2011; which claims the benefit under 35 U.S.C. 119(a) of United Kingdom Application Serial No. 0807615.0, filed Apr. 25, 2008; each of which are hereby incorporated by reference into this application in their entirety.

BACKGROUND OF THE INVENTION

Field of the Invention

The present invention relates to the synthesis of deoxycholoic acid and, pharmaceutically acceptable salts and intermediates thereof.

State of the Art

Rapid removal of body fat is an age-old ideal, and many substances have been claimed to accomplish such results, although few have shown results. "Mesotherapy", or the use of injectables for the removal of fat, is not widely accepted among medical practitioners due to safety and efficacy concerns, although homeopathic and cosmetic claims have been made since the 1950's. Mesotherapy was originally conceived in Europe as a method of utilizing cutaneous injections containing a mixture of compounds for the treatment of local medical and cosmetic conditions. Although mesotherapy was traditionally employed for pain relief, its cosmetic applications, particularly fat and cellulite removal, have recently received attention in the United States. One such reported treatment for localized fat reduction, which was popularized in Brazil and uses injections of phosphatidylcholine, has been erroneously considered synonymous with mesotherapy. Despite its attraction as a purported "fat-dissolving" injection, the safety and efficacy of these cosmetic treatments remain ambiguous to most patients and physicians. See, Rotunda, A. M. and M. Kolodney, Dermatologic Surgery 32: 465-480 (2006) ("Mesotherapy and Phosphatidylcholine Injections: Historical Clarification and Review").

Recently published literature reports that the bile acid deoxycholic acid has fat removing properties when injected into fatty deposits in vivo. See, WO 2005/117900 and WO 2005/112942, as well as US2005/0261258; US2005/0267080; US2006/127468; and US20060154906, all incorporated herein by reference in their entirety including figures). Deoxycholate injected into fat tissue has the effects of: 1) degrading fat cells via a cytolytic mechanism; and 2) causing skin tightening. Both of these effects are required to mediate the desired aesthetic corrections (i.e., body contouring). Because deoxycholate injected into fat is rapidly inactivated by exposure to protein and then rapidly returns to the intestinal contents, its effects are spatially contained. As a result of this attenuation effect that confers clinical safety, fat removal therapies typically require 4-6 sessions. This localized fat removal without the need for surgery is beneficial not only for therapeutic treatment relating to pathological localized fat deposits (e.g., dyslipidemias incident to medical intervention in the treatment of HIV), but also for cosmetic fat removal without the attendant risk inherent in surgery (e.g., liposuction). See, Rotunda et al., Dermatol. Surgery 30: 1001-1008 (2004) ("Detergent effects of sodium deoxycholate are a major feature of an injectable phosphatidylcholine formulation used for localized fat dissolution") and Rotunda et al., J. Am. Acad. Dermatol. (2005: 973-978) ("Lipomas treated with subcutaneous deoxycholate injections"), both incorporated herein by reference.

Pharmaceutical grade bile acid preparations are commercially available at relatively low cost. This low cost is due to the fact that the bile acids are obtained from animal carcasses, particularly large animals such as cows and sheep. Importantly, as with all medicaments from animal sources, there is concern that the animal-derived bile acid products may contain animal pathogens and other harmful agents such as animal or microbial metabolites and toxins, including bacterial toxins such as pyrogens.

Currently, the concerns regarding animal-derived products containing animal pathogens and other harmful agents has been addressed by sourcing from isolated and inspected animals. For example, deoxycholic acid from animals in New Zealand are a source of bile acids for human use under US regulatory regimes, as long as the animals continue to remain isolated and otherwise free of observable pathogens.

There remains a need for suitable quantities of efficacious bile acids such as deoxycholic acids that are known from the outset to be free from moieties of animal origin (or pathogenic moieties capable of acting in an animal, particularly a mammal, and for human use, having a deleterious effect on a human), and other harmful agents such as animal or microbial metabolites, toxins, including bacterial toxins, such as pyrogens, for use as medicaments in humans.

SUMMARY OF THE INVENTION

The present invention provides methods and intermediates relating to the synthesis of deoxycholic acid and pharmaceutically acceptable salts thereof. The synthetically prepared deoxycholic acid can be used in adipolytic therapy for fat removal.

BRIEF DESCRIPTION OF THE FIGURE

FIG. 1 shows the similarity in dose-dependent decrease in cell survival of primary human adipocytes upon treatment with synthetic sodium deoxycholic acid of the present invention in comparison to bovine-derived sodium deoxycholate (Sigma).

DETAILED DESCRIPTION OF THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

As used herein, certain terms may have the following defined meanings. As used in the specification and claims, the singular form "a," "an" and "the" include singular and plural references unless the context clearly dictates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques.

As used herein, the term "comprising" is intended to mean that the compounds and methods include the recited elements, but not excluding others. "Consisting essentially of when used to define compositions and methods, shall mean excluding other elements of any essential significance to the compounds or method." Consisting of shall mean excluding more than trace elements of other ingredients for claimed compounds and substantial method steps. Embodiments defined by each of these transition terms are within the scope of this invention. Accordingly, it is intended that the methods and compounds can include additional steps and components (comprising) or alternatively include additional steps and compounds of no significance (consisting essentially of) or alternatively, intending only the stated methods steps or compounds (consisting of).

The term "alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "oxidizing agent" refers to a reagent which can accept electrons in an oxidation-reduction reaction. In this way, oxygen can be added to a molecule or hydrogen can be removed from a molecule.

The term "reducing agent" refers to a reagent which can donate electrons in an oxidation-reduction reaction, allowing hydrogen to be added to a molecule.

The term "acetylating reagent" refers to a reagent in which can add an acetyl (Ac) group $CH_3C(O)$— to an alcohol moiety of a molecule.

The term "acid" refers to regents capable of donating $H^+$.

The term "Lewis acid" refers to an electron pair acceptor. Lewis acids include oraganometallic reagents such as alkyl aluminum halides (e.g. $Et_2AlCl$ and $MeAlCl_2$).

The term "hydrogenation conditions" refers to suitable conditions and catalysts for introducing $H_2$ across one or more double bonds. Hydrogenation catalysts include those based on platinum group metals (platinum, palladium, rhodium, and ruthenium) such as Pd/C and $PtO_2$.

The term "olefination reagent" refers to regents that react with ketones to form the corresponding olefins. The term "olefin forming conditions" refers to suitable conditions for carryout such transformations. Examples of such reagents include Wittig regeants and Wittig olefination conditions.

The numbering of the steroidal scaffold as used herein follows the general convention:

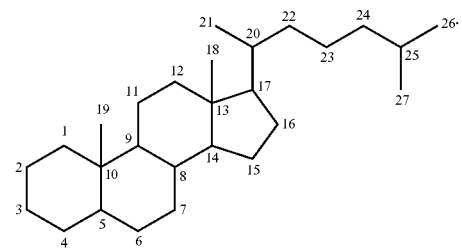

Accordingly, provided is a method for preparing deoxycholic acid (DCA) or a pharmaceutically acceptable salt thereof:

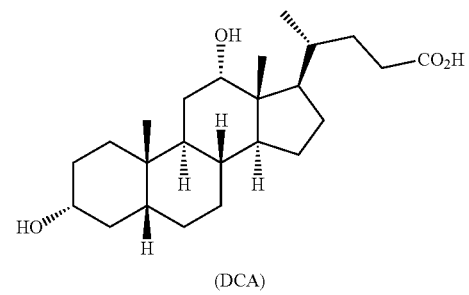

(DCA)

said method comprising
(a) reacting 9α-hydroxyandrost-4-en-3,17-dione 1.0 with $H_2$ under hydrogenation conditions to form compound 1.1

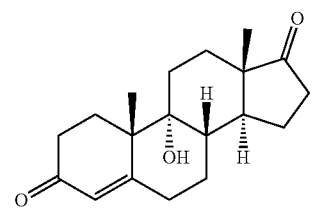

1.0

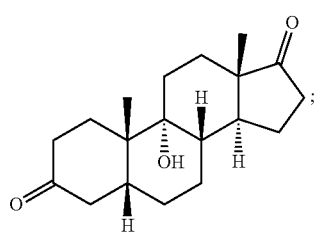

1.1

(b) reacting compound 1.1 with acid to form compound 1.2

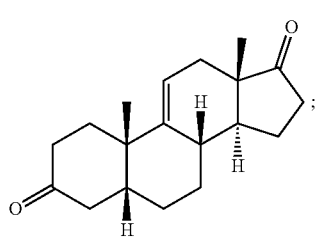

1.2

(c) reacting compound 1.2 a reducing agent to form compound 1.3 a mixture of 1.3 and 1.4

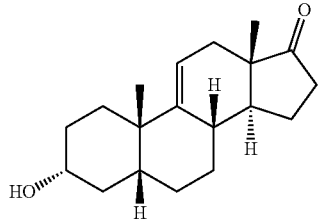

1.3

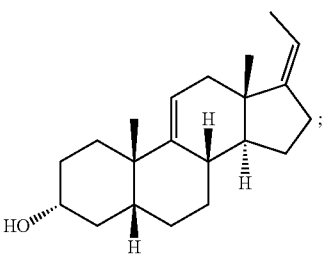

1.4

(d) reacting compound 1.3 with a two carbon olefination reagent under olefin forming conditions to form compound 1.5

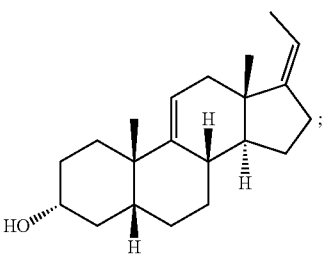

1.5

(e) converting compound 1.5 to a compound of formula 1.6 wherein P is a protecting group

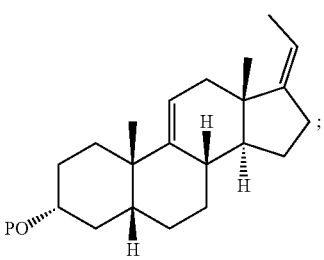

1.6

(f) reacting a compound of formula 1.6 with an alkylpropiolate CH₂CH₂C(O)OR or an alkyl acrylate CH₂=CHC(O)OR wherein R is alkyl in the presence of a Lewis acid to form a compound of formula 1.7 wherein P is a protecting group, R is a alkyl, and the dashed line ==== is a single or double bond;

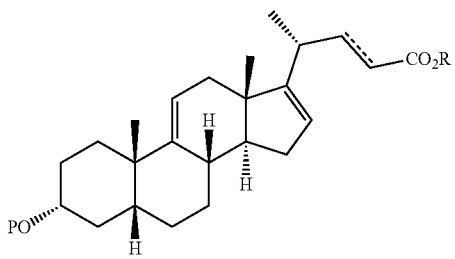

1.7

(g) reacting a compound of formula 1.7 with H₂ under hydrogenation conditions to form a compound of formula 1.8 wherein P is a protecting group and R is alkyl

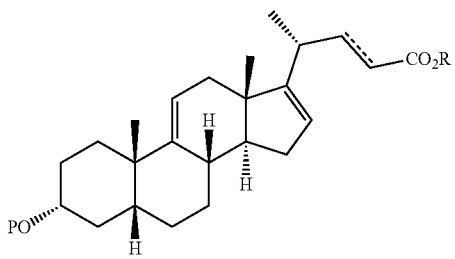

1.8

(h) reacting compound of formula 1.8 with an oxidizing agent to form a compound of formula 1.9 wherein P is a protecting group and R is alkyl

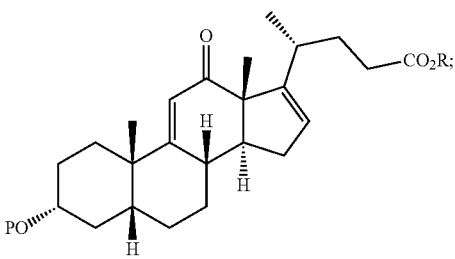

1.9

(i) reacting a compound of formula 1.9 with H₂ under hydrogenation conditions to form compound of formula 2.0 wherein P is a protecting group and R is alkyl

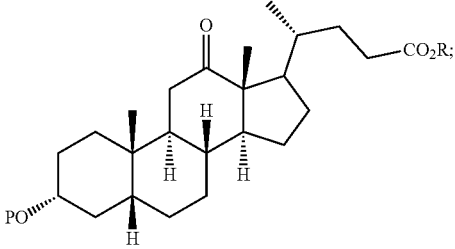

2.0

(j) reacting compound of formula 2.0 with a reducing agent to form a compound of formula 2.1 wherein P is a protecting group and R is alkyl

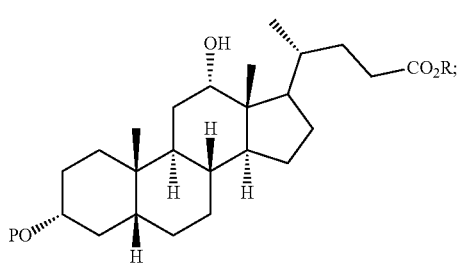
2.1
and
(k) exposing compound of formula 2.1 to deprotection and hydrolysis conditions to form deoxycholic acid.
The present invention also provides the following intermediates shown in Scheme 1 below wherein Ac and R are as defined above.
Scheme 1. Synthesis of Deoxycholic Acid (DCA)
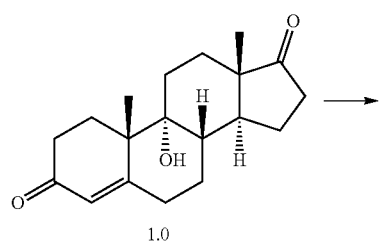
1.0
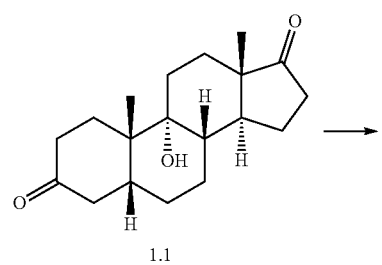
1.1
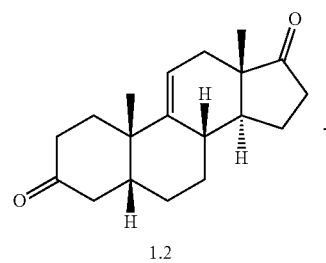
1.2
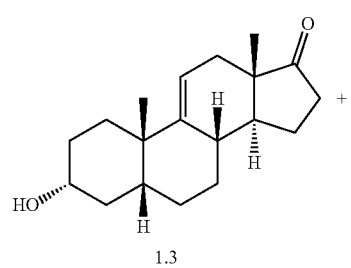
1.3
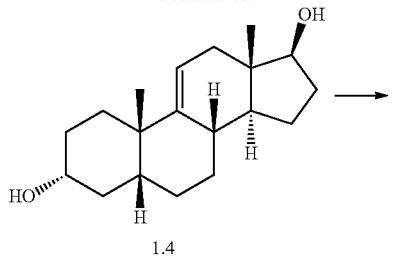
1.4
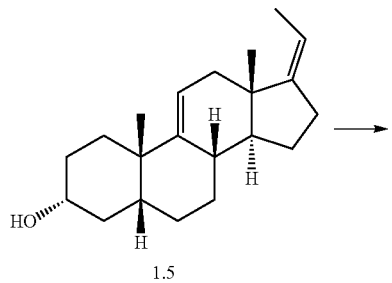
1.5
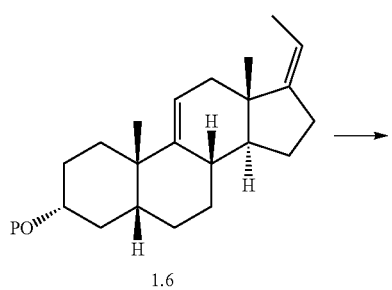
1.6
1.6a P = Ac
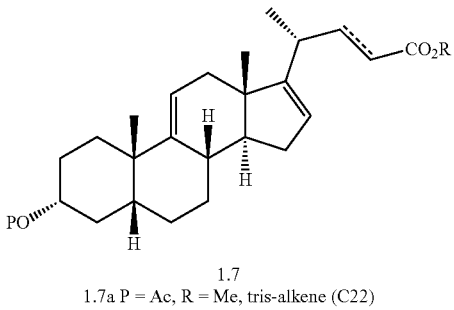
1.7
1.7a P = Ac, R = Me, tris-alkene (C22)
1.7b P = Ac, R = Me bis-alkene
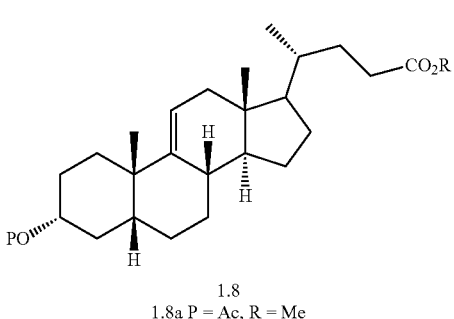
1.8
1.8a P = Ac, R = Me

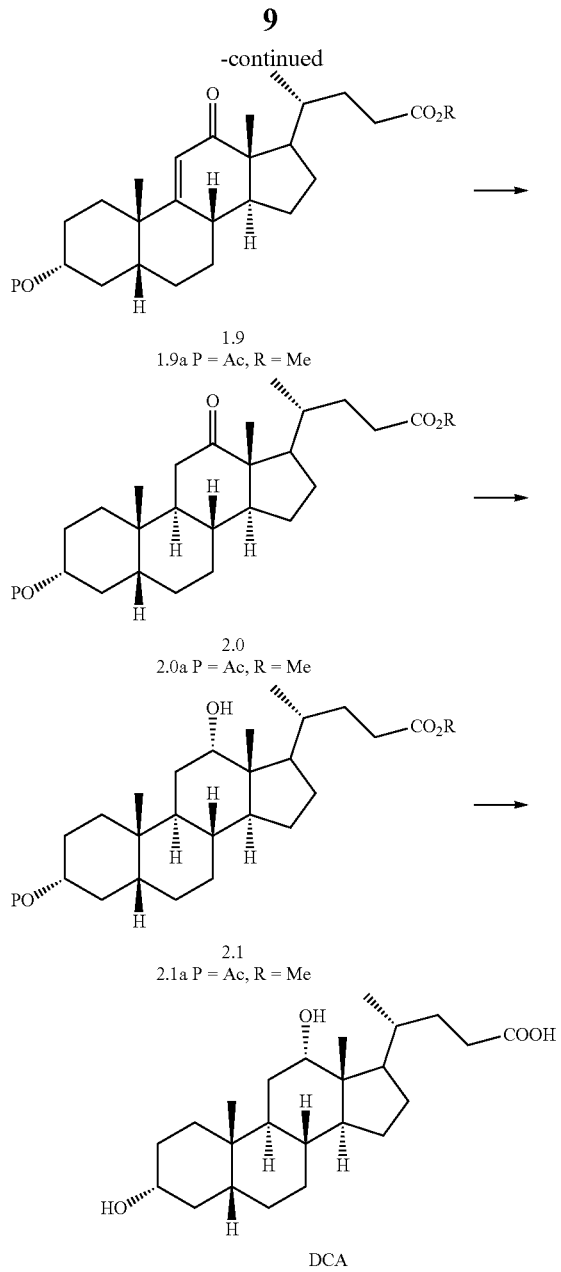

In one embodiment, the oxidizing agent of part (h) is $CrO_3$.

In one embodiment, the hydrogenation conditions of part (i) comprises a Pd/C catalyst.

In one embodiment, the reducing agent of part (j) is $LiAl(OtBu)_3H$.

In one embodiment, the deprotection and hydrolysis conditions of part (k) when P is —C(O)CH₃ comprises reacting compound 2.1a with an alkali earth hydroxide, alkali earth alkoxide, or a mixture of both.

In one embodiment, the alkali earth alkoxide is LiOH.

In one embodiment, salts of deocycholoic acid can be prepared by reaction with an alkali earth metal alkoxide or hydroxide. Salts of deocycholoic acid include the sodium ($Na^+$), potassium ($K^+$), and lithium ($Li^+$) salts.

In one embodiment, provided is an intermediate compound selected from the group consisting of
9α-Hydroxy-5β-androstan-3,17-dione (1.1);
5β-Androst-9(11)-en-3,17-dione (1.2);
(Z)-3α-Hydroxy-5β-pregna-9(11),17(20)-diene (1.5);
(Z)-3α-Acetoxy-5β-pregna-9(11),17(20)-diene (1.6);
(E)-Methyl 3α-acetoxy-5β-chol-9(11), 16, 22-trien-24-oate (1.7a);
Methyl 3α-acetoxy-5β-chol-9(11), 16-dien-24-oate (1.7b);
Methyl 3α-hydroxy-5β-chol-9(11)-en-12-one-24-oate (1.9a); and
Methyl 3α-acetoxy-5β-cholan-12-one-24-oate (2.0a).

The compounds of preferred embodiments can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

The starting materials and reagents for the reactions described herein are generally known compounds or can be prepared by known procedures or obvious modifications thereof. For example, many of the starting materials and reagents are available from commercial suppliers such as Aldrich Chemical Co. (Milwaukee, Wis., USA), Bachem (Torrance, Calif., USA), Emka-Chem or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4th Edition), and Larock's *Comprehensive Organic Transformations* (VCH Publishers Inc., 1989).

The various starting materials, intermediates, and compounds of the preferred embodiments may be isolated and purified where appropriate using conventional techniques In one embodiment, the hydrogenation conditions of part (a) comprises a Pd/C catalyst.

In one embodiment, the acid of part (b) is a mineral acid. In some aspects, the mineral acid is $H_2SO_4$.

In one embodiment, the reducing agent of part (c) is $LiAl(OtBu)_3H$.

In one embodiment, the two carbon olefination reagent of part (d) is a Wittig agent such as $Ph_3PCH_2CH_3^+Br^-$.

In one embodiment, the protecting group P of compound 1.6-2.1 is —C(O)CH₃. In some aspects compound 1.5 is exposed to acylation conditions to form 1.6a, such as by treatment of 1.5 with acetic anhydride and an organic base such as Et₃N, pyridine, and/or dimethylaminopyridine.

In one embodiment, the Lewis acid of part (f) is $EtAlCl_2$.

In one embodiment, the alkylpropiolate of part (f) is methylpropriolate.

In one embodiment, the alkyl acrylate of part (f) is methylacrylate.

In one embodiment, the hydrogenation conditions of part (g) comprises a $PtO_2$ or Pd/C catalyst.

such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

The foregoing and other aspects of the embodiments disclosed herein may be better understood in connection with the following examples.

EXAMPLES

In the examples below and elsewhere in the specification, the following abbreviations have the indicated meanings. If an abbreviation is not defined, it has its generally accepted meaning.

| | |
|---|---|
| AcOH | Acetic acid |
| Ac$_2$O | Acetic anhydride |
| CrO$_3$ | Chromium trioxide |
| DCA | Deoxycholic acid |
| DCM (CH$_2$Cl$_2$) | Dichloromethane |
| DMF | N,N-Dimethylformamide |
| EtOAc | Ethyl acetate |
| EtAlCl$_2$ | Ethyl aluminum dichloride |
| Hz | Hertz |
| HPLC | High pressure liquid chromatography |
| HCl | Hydrochloric acid |
| LiOH | Lithium hydroxide |
| Na$_2$SO$_4$ | Sodium sulfate |
| MHz | Megahertz |
| min | Minutes |
| MeOH | Methanol |
| mmol | millimole |
| mL | milliliter |
| mol | mole |
| Obs | Observed |
| HClO$_4$ | Perchloric acid |
| PtO$_2$ | Platinum oxide |
| Pd/C | Palladium on carbon |
| H$_2$SO$_4$ | Sulphuric acid |
| DMAP | 4-Dimethylaminopyridine |
| LiAl(O$^t$Bu)$_3$H | Lithium tri-tert-butoxyaluminum hydride |
| KBr | Potassium bromide |
| K-O$^t$Bu | Potassium tert-butoxide |
| Rep | Reported |
| NaOH | Sodium hydroxide |
| THF | Tetrahydrofuran |
| TEA | Triethylamine |
| TLC | Thin layer chromatography |
| Wt | Weight |
| CONC | Concentrated |
| ACN | Acetonitrile |
| TFA | Trifluoroacetic acid |

General: All manipulations of oxygen- and moisture-sensitive materials were conducted with standard two-necked flame dried flasks under an argon or nitrogen atmosphere. Column chromatography was performed using silica gel (60-120 mesh). Analytical thin layer chromatography (TLC) was performed on Merck Kiesinger 60 F$_{254}$ (0.25 mm) plates. Visualization of spots was either by UV light (254 nm) or by charring with a solution of sulfuric acid (5%) and p-anisaldehyde (3%) in ethanol.

Apparatus: Proton and carbon-13 nuclear magnetic resonance spectra CH NMR and $^{13}$C NMR) were recorded on a Varian Mercury-Gemini 200 ($^1$H NMR, 200 MHz; $^{13}$C NMR, 50 MHz) or a Varian Mercury-Inova 500 NMR, 500 MHz; $^{13}$C NMR, 125 MHz) spectrometer with solvent resonances as the internal standards CH NMR, CHCl$_3$ at 7.26 ppm or DMSO at 2.5 ppm and DMSO-H$_2$O at 3.33 ppm; $^{13}$C NMR, CDCl$_3$ at 77.0 ppm or DMSO at 39.5 ppm). $^1$H NMR data are reported as follows: chemical shift (δ, ppm), multiplicity (s=singlet, d=doublet, t=triplet, q=quartet, br=broad, m=multiplet), coupling constants (Hz), and integration. Infrared spectra (FT-IR) were run on a JASCO-460$^+$ model. Mass spectra were obtained with a Perkin Elmer API-2000 spectrometer using ES$^+$ mode. Melting points were determined using a LAB-INDIA melting point measuring apparatus and are uncorrected. HPLC chromatograms were recorded using a SHIMADZU-2010 model with a PDA detector. Specific optical rotations were determined employing a JASCO-1020 at 589 nm and are uncorrected.

Chemicals: Unless otherwise noted, commercially available reagents were used without purification. Diethyl ether and THF were distilled from sodium/benzophenone. Laboratory grade anhydrous DMF, commercially available DCM, ethyl acetate and hexane were used.

Example 1

9α-Hydroxy-5β-androstan-3,17-dione (1.1)

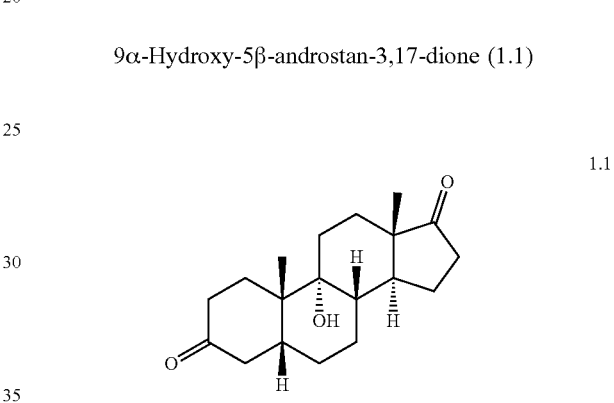

1.1

To a solution of 9α-hydroxyandrost-4-en-3,17-dione 1.0 (30.0 g, 99.3 mol) in DMF (150 mL) was added 10% of Pd/C (2.1 g) and the resulting slurry was hydrogenated in a Parr apparatus (60 psi) for 12 h. Upon complete disappearance of starting material, as evidenced by TLC, the crude reaction mixture was filtered through a small pad of CELITE® (diatomaceous earth), and the solvent was removed under vacuum to provide a colorless solid (30.0 g). This solid was combined with acetone (90 mL.) at 0° C. and the resulting slurry was stirred for 1 h. It was then filtered, washed with chilled (0° C.) acetone (30 mL) and dried under vacuum in the same filtration funnel at room temperature to afford compound 1.1 (26.0 g, 86%).

TLC: p-anisaldehyde charring, R$_f$ for 1.1=0.48 and R$_f$ for 1.0=0.30.

TLC mobile phase: 30%-EtOAc in DCM.

NMR (500 MHz, CDCl$_3$): δ=2.37-2.40 (m, 1H), 2.02-2.11 (m, 2H), 1.31-1.91 (m, 19H), 0.96 (s, 3H), 0.84 (s, 3H).

$^{13}$C NMR (125 MHz, CDCl$_3$): δ=221.0, 95.7, 80.1, 47.0, 43.6, 38.6, 38.5, 37.1, 35.9, 33.41, 32.9, 32.0, 27.9, 26.9, 21.5, 20.2, 20.0, 12.6.

Mass (m/z)=305.0[M$^+$+1], 322.0 [M$^+$+18].

IR (KBr)=3443, 2938, 1722, 1449, 1331, 1138 cm$^1$.

m.p=213-216° C. (from DMF and acetone)

[α]$_D$=+116 (c=1% in CHCl$_3$).

ELSD Purity: more than 99%, ret. time=8.15, 9-HAD ret. time=3.88, 5α-isomer of Cmpd 121 ret. time=4.91 (Water symmetry 250×4.6 mm, 5 um, C18), Water:ACN (40:60).

Example 2

5β-Androst-9(11)-en-3,17-dione (1.2)

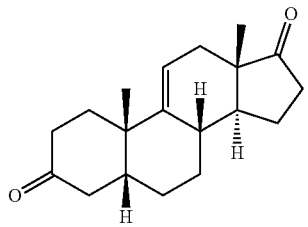

To a solution of compound 1.1 (26.0 g, 85.4 mmol) in DCM (520 mL) was added concentrated sulfuric acid (7.53 g, 76.8 mmol) over 15 minutes under an inert atmosphere at 10° C. The temperature was raised to 25° C. and the resulting solution was stirred for 2 h. At this point no more starting material remained as evidenced by TLC. The reaction was quenched by the addition of 10% aqueous $NaHCO_3$ solution (200 mL). The layers were separated and the aqueous layer was extracted twice with DCM (2×100 mL). The organic layers were combined and washed sequentially with water (100 mL) and saturated brine solution (100 mL). The organic phase was then dried over $Na_2SO_4$ (75 g) and filtered. The filtrate was evaporated under vacuum to provide compound 1.2 (23.0 g, 94%) as an off-white solid. This product was used "as is" in the next step without further purification.

TLC: p-anisaldehyde charring, $R_f$ for 1.2=0.76 and $R_f$ for 1.1=0.44.

TLC mobile phase: 30%-EtOAc in DCM.

$^1$H NMR (500 MHz, $CDCl_3$): δ=5.61 (s, 1H), 2.47-2.57 (m, 2H), 2.24-2.42 (m, 4H), 2.05-2.20 (m, 3H), 1.86-1.99 (m, 2H), 1.84-1.85 (d, J=6 Hz 1H), 1.57-1.63 (m, 5H), 1.37-1.40 (d, J=13.5 Hz, 1H) 1.25-1.28 (dd, J=4.0, 13.5 Hz, 1H), 1.17 (s, 3H) 0.85 (s, 3H).

$^{13}$C NMR (125 MHz, $CDCl_3$): δ=221.3, 212.8, 140.1, 118.5, 48.5, 45.9, 44.3, 43.5, 39.0, 38.0, 37.3, 36.1, 35.8, 33.3, 28.8, 26.0, 25.5, 22.5, 13.9.

Mass (m/z)=287 [M$^+$+1], 304 [+18].

IR (KBr)=3450, 2913, 1737, 1707, 1413, 1403, 1207 cm$^{-1}$.

m.p.=143.4-145.9° C. (from DCM)

$[α]_D$=+142 (c=1% in $CHCl_3$).

ELSD Purity: 99.7%, Retention time=5.04, (Inertsil ODS 3V 250×4.6 mm, 5 um), ACN: 0.1% TFA in water (90:10).

Example 3

3α-Hydroxy-5β-androst-9(11)-en-17-one (1.3)

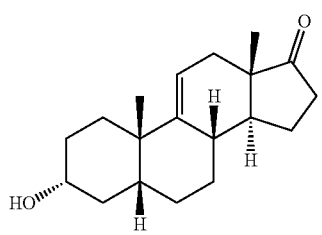

A THF solution of lithium tri-tert-butoxyaluminum hydride (1.0 M, 84.4 mL, 84.4 mmol) was added to a cold (−40° C.) solution of compound 1.2 (23.0 g, 80.4 mmol) in THF (230 mL) under an inert atmosphere. The resulting reaction mixture was stirred for 2 h. At this point the reaction was determined to be complete, as evidenced by TLC, and the reaction mixture was quenched by adding a mixture of 1N HCl (200 mL) and ethyl acetate (230 mL). The resulting two phase mixture was separated and the aqueous layer was extracted twice with ethyl acetate (2×100 mL). The organic phases were combined and washed sequentially with water (150 mL) and saturated brine solution (100 mL). The organic phase was then dried over $Na_2SO_4$ (75 g) and filtered. The filtrate was evaporated under vacuum to afford compound 1.3 (23.0 g) as an off-white solid. The above crude product was used "as is" in the next step without purification.

TLC: p-anisaldehyde charring, $R_f$ for 1.3=0.44 and $R_f$ for 1.2=0.74.

TLC mobile phase: 30%-EtOAc in DCM (30%).

$^1$H NMR (500 MHz, $CDCl_3$): δ=5.41-5.42 (d, J=6.0 Hz, 1H), 3.65-3.66 (m, 1H), 2.43-2.48 (m, 1H), 1.98-2.18 (m, 6H), 1.74 (s, 2H), 1.48-1.56 (m, 5H), 1.377-1.45 (m, 3H), 1.18-1.28 (m, 3H), 1.08 (s, 3H), 0.80 (s, 3H)

$^{13}$C NMR (125 MHz, $CDCl_3$): δ=222.0, 140.9, 118.3, 71.9, 48.6, 45.9, 41.7, 38.8, 37.8, 36.2, 36.0, 35.7, 33.4, 31.7, 29.5, 26.5, 26.0, 22.7, 13.9.

Mass (m/z)=289.0 [M$^+$+1], 306.0 [M$^+$+18].

IR (KBr)=3463, 2960, 2871, 1729, 1366, 1165, 1084, 1041 cm$^1$.

m.p.=165-167.5° C. (EtOAc/hexanes mixture).

$[α]_D$=+161 (c=1% in $CHCl_3$).

ELSD Purity: ~93%, Retention time=5.23, (Inertsil ODS 3V 250×4.6 mm, 5 um), ACN: 0.1% TFA in water (90:10).

Example 4

(Z)-3α-Hydroxy-5β-pregna-9(11),17(20)-diene (1.5)

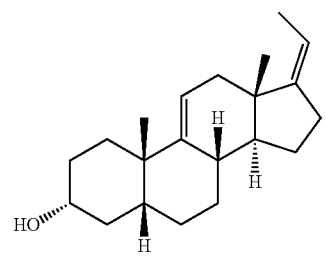

A solution of potassium tert-butoxide in THF (1 M, 230 mL, 231 mmol) was added drop wise to a suspension of ethyltriphenylphosphonium bromide (88.7 g, 239 mmol) in THF (150 mL) over 1 h at 25° C. The resulting dark red colored mixture was stirred for an additional 1 h at 25° C. A solution of compound 1.3 (23.0 g, 79.7 mmol) in THF (230 mL) was added slowly to the red-colored mixture at 25° C. The resulting mixture was stirred for 3-4 h, at which point it was determined to be complete by TLC. The reaction was quenched by adding saturated aqueous $NH_4Cl$ solution (75 mL). The phases were separated and the aqueous layer was extracted three times with EtOAc (3×150 mL). The organic fractions were combined, washed with saturated brine solution (100 mL), dried over $Na_2SO_4$ (75 g), and filtered. The filtrate was concentrated under vacuum and the crude solid was purified by column chromatography [49 mm (W)×600 mm (L), 60-120 mesh silica, 300 g] eluting with ethyl acetate/hexanes (1:9). The fractions containing product were combined and concentrated, providing compound 1.5 (19.1 g, 80.0%) as a white solid.

TLC: p-anisaldehyde charring, $R_f$ for 1.5=0.72 and $R_f$ for 1.3=0.46.

TLC mobile phase: 30%-EtOAc in DCM.

$^1$H NMR (500 MHz, CDCl$_3$): δ=5.38 (s, 1H), 5.18-5.19 (d, J=6.5 Hz 1H), 3.62-3.66 (m, 1H), 2.35-2.38 (d, J=15 Hz, 3H), 2.23-2.25 (m, 1H), 1.97-2.07 (m, 3H), 1.64-1.75 (m, 6H), 1.32-1.55 (m, 6H), 1.17-1.24 (m, 4H), 1.06 (s, 3H), 0.79 (s, 3H).

$^{13}$CNMR (125 MHz, CDCl$_3$): δ=150.1, 140.6, 119.6, 114.2, 72.2, 53.6, 42.0, 41.9, 39.6, 38.6, 37.9, 35.7, 35.6, 31.9, 31.8, 29.5, 26.9, 26.8, 25.5, 16.9, 13.3.

Mass (m/z)=301[W+1], 318[W+18].

IR (CHCl$_3$)=3304, 3033, 2925, 2863, 1449, 1368, 1040, 823 cm$^{-1}$.

mp=146-147.3° C. (EtOAc/hexanes mixture).

[α]$_D$=+84.4 (c=1% in CHCl$_3$).

ELSD Purity: 99.8%, Retention time=16.07, (Inertsil ODS 3V 250×4.6 mm, 5 um), ACN: 0.1% TFA in water (90:10).

Example 5

(Z)-3α-Acetoxy-5β-pregna-9(11),17(20)-diene (1.6a)

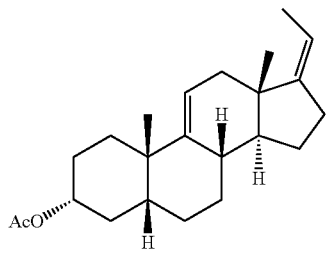

Compound 1.5 (19.0 g, 63 mmol) was dissolved in CH$_2$Cl2 (380 mL). Triethylamine (17.6 mL, 126.6 mmol), DMAP (0.772 g, 6 mmol) and acetic anhydride (8.98 mL, 94 mmol) were added sequentially at 25° C. under a nitrogen atmosphere. The resulting solution was stirred for 2 h at 25° C., at which point the reaction was determined by TLC to be complete. The reaction was quenched by the addition of ice-water (100 mL) and the phases were separated. The aqueous layer was extracted three times with DCM (3×150 mL). The organic fractions were combined and washed with saturated brine solution (100 mL), dried over anhydrous Na$_2$SO$_4$ (50 g), and filtered. The filtrate was concentrated under vacuum to afford compound 1.6a (22.0 g, 95% yield) as an off-white solid.

TLC: p-anisaldehyde charring, $R_f$ for 1.6=0.5 and $R_f$ for 1.5=0.15.

TLC mobile phase: 10%-EtOAc in hexanes.

$^1$H NMR (500 MHz, CDCl$_3$): δ=5.38 (s, 1H), 5.18-5.20 (d, J=6.5 Hz, 1H), 4.72-4.76 (m, 1H), 2.35-2.40 (m, 3H), 2.22-2.25 (m, 1H), 2.03-2.09 (m, 3H), 2.01 (s, 3H), 1.49-1.98 (m, 10H), 1.31-1.41 (m, 2H), 1.16-1.27 (m, 3H), 1.07 (s, 3H), 0.79 (s, 3H).

$^{13}$C NMR (125 MHz, CDCl$_3$): δ=170.5, 150.0, 140.4, 119.6, 114.3, 74.7, 53.5, 42.0, 41.7, 39.6, 38.6, 35.6, 35.3, 33.8, 31.9, 29.5, 27.8, 26.7, 26.6, 25.5, 21.3, 16.9, 13.2 Mass (m/z)=342.9 [M$^+$+1], 360 [M$^+$+18].

IR (CHCl$_3$)=3440, 3035, 1730, 1451, 1367, 1258, 1028 cm$^{-1}$.

mp=93.9-97.8° C. (EtOAc/hexanes mixture)

[α]$_D$=+109 (c=1% in CHCl$_3$).

HPLC purity: 97.62%; Retention time=17.7, (Zorbax SB, C18; 250×4.6 mm, 5 um), ACN: 0.1% TFA in water (90:10).

Example 6

(E)-Methyl 3α-acetoxy-5β-chol-9(11), 16, 22-trien-24-oate (1.7a)

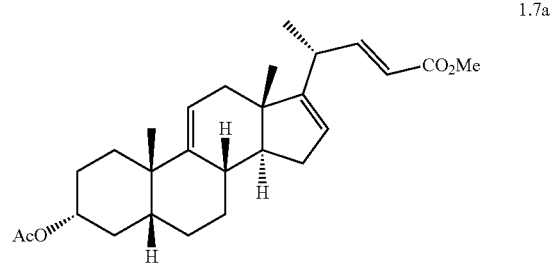

Ethyl aluminum dichloride (104.5 mL, 192 mmol, 1.8 M in toluene) was added to a solution of methyl propiolate (13.58 mL, 153 mmol) in DCM (100 mL) at 0° C. under inert atmosphere. The resulting solution was stirred for 15 min and then compound 1.6a (22 g, 64.3 mmol) was added. After stirring for an additional 20 min at 0° C., the temperature was raised to 25° C. and held there for a further 18 h. At this point the reaction was determined to be complete by TLC, and the mixture was poured into cold (0° C.) water (200 mL). The phases were separated and the aqueous layer was extracted with DCM (150 mL). The organic layers were combined and washed sequentially with water (200 mL) and saturated brine solution (100 mL). It was then dried over anhydrous Na$_2$SO$_4$ (40 g) and filtered. The filtrate was concentrated under vacuum and the resulting solid was purified by slurring in methanol (280 mL) to provide compound 1.7a (17.5 g 68%) as a white solid.

TLC: p-anisaldehyde charring, $R_f$ for 1.7a=0.32 and $R_f$ for 1.6a=0.5.

TLC mobile phase: 10%-EtOAc in hexanes.

NMR (500 MHz, CDCl$_3$): δ=6.92-6.926 (q, J=7.5, 15.5 Hz, 1H), 5.80-5.83 (d, J=16 Hz, 1H), 5.37-5.43 (m, 2H), 4.73-4.75 (m, 1H), 3.73 (s, 3H), 3.02-3.04 (t, J=6.5 Hz, 1H), 2.15-2.23 (m, 3H), 2.05-2.08 (m, 3H), 2.01 (s, 3H), 1.48-1.99 (m, 8H), 1.24-1.34 (m, 2H), 1.20-1.21 (d, J=5 Hz, 3H), 1.11-1.17 (m, 1H), 1.07 (s, 3H), 0.67 (s, 3H).

$^{13}$C NMR (125 MHz, CDCl$_3$): δ=170.5, 167.2, 155.0, 153.7, 141.6, 124.0, 118.8, 118.7, 74.6, 53.9, 51.3, 45.7, 41.7, 38.8, 37.1, 35.5, 35.3, 34.6, 33.7, 31.8, 29.5, 27.7, 26.5, 26.5, 21.3, 19.7, 15.7.

Mass (m/z)=444.0 [M$^+$+18].

IR (KBr)=3443, 3030, 2930, 1719, 1650, 1247, 1359, 1032, 1170 cm$^{-1}$.

m.p.=114-116° C. (from methanol)

[α]$_D$=+102 (c=1% in CHCl$_3$).

ELSD Purity: 99.7%, Retention time=19.57, (Inertsil ODS 3V 250×4.6 mm, 5 um), ACN: 0.1% TFA in water (90:10).

Example 7

Methyl 3α-acetoxy-5β-chol-9(11)-en-24-oate (1.8a)

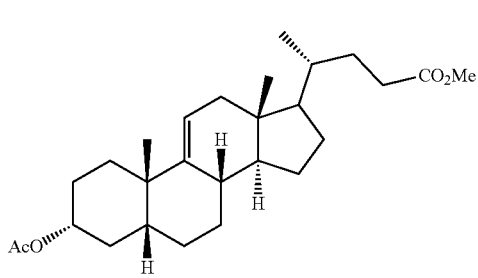

1.8a

To a solution of compound 1.7a (17.5 g, 41 mmol) in EtOAc (350 mL) was added PtO$_2$ (4.37 g), and the resulting slurry was hydrogenated in a Parr apparatus (70 psi) for 14-16 h. At this point the reaction was determined to be complete by TLC. The mixture was filtered through a small plug of CELITE® (diatomaceous earth) and the solvent was removed under vacuum, affording compound 1.8a (17.0 g, 96.0%) as a white solid. The above product was used in the next step without further purification.

TLC: p-anisaldehyde charring, R$_f$ for 1.8a=0.32 and R$_f$ for 1.7a=0.30.

TLC mobile phase: 10%-EtOAc in hexanes.

$^1$H NMR (500 MHz, CDCl$_3$): δ=5.31 (s, 1H), 4.73 (m, 1H), 3.66 (s, 3H), 2.03-2.37 (m, 7H), 2.01 (s, 3H), 1.09-1.98 (m, 18H), 1.06 (s, 3H), 0.91-0.92 (d, J=6.0 Hz, 3H), 0.59 (s, 3H).

$^{13}$C NMR (125 MHz, CDCl$_3$): δ=174.6, 170.5, 139.8, 119.5, 74.8, 56.0, 53.3, 51.4, 41.9, 41.7, 40.9, 38.5, 36.4, 35.4, 35.2, 33.8, 31.0, 30.9, 29.5, 28.2, 27.8, 26.8, 26.7, 25.2, 21.4, 17.9, 11.5

Mass (m/z)=448.2 [M$^+$+18].

IR (KBr)=3435, 3039, 2941, 1729, 1448, 1435, 1252, 1022 cm$^{-1}$.

m.p.=122.1-123.9° C. (from EtOAc).

[α]$_D$=+56 (c=1% in CHCl$_3$)

ELSD Purity: 97.7%: Retention time=14.57 (ZORBAX SB C-18 150×4.6 mm, 5 um, ACN: 0.1% TFA in water (90:10)

Example 8

Methyl 3α-acetoxy-5β-chol-9(11), 16-dien-24-oate (1.7b)

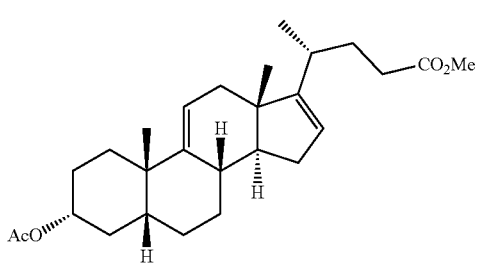

1.7b

Ethyl aluminum dichloride (14.2 mL, 25 mmol, 1.8M in toluene) was added to a solution of methyl acrylate (1.89 mL, 20 mmol) in DCM (60 mL) at 0° C. under inert atmosphere. The resulting solution was stirred for 15 min and then compound 1.6a (3 g, 8.7 mmol) was added. After stirring for an additional 20 min at 0° C., the temperature was raised to 25° C. and held there for a further 18 h. At this point the reaction was determined to be complete by TLC, then the mixture was poured into cold (0° C.) water (60 mL). The phases were separated and the aqueous layer was extracted with DCM (60 mL). The organic layers were combined and washed sequentially with water (50 mL) and saturated brine solution (100 mL). It was then dried over anhydrous Na$_2$SO$_4$ (5 g) and filtered. The filtrate was concentrated under vacuum, providing compound 1.7b (2.6 g, 70%).

TLC mobile phase: 10%-EtOAc in hexanes.

$^1$H NMR (500 MHz, CDCl$_3$): δ=5.34-5.43 (m, 2H), 4.73-4.75 (m, 1H), 3.73 (s, 3H), 2.15-2.34 (m, 6H), 2.05-2.08 (m, 3H), 2.01 (s, 3H), 1.48-1.99 (m, 9H), 1.24-1.34 (m, 3H), 1.20-1.21 (d, J=5 Hz, 3H), 1.11-1.17 (m, 1H), 1.07 (s, 3H), 0.67 (s, 3H).

ELSD Purity: 93.9%, ret. time=4.55, (Water symmetry shield 250×4.6 mm ACN:100%

Example 9

Methyl 3α-acetoxy-5β-chol-9(11)-en-24-oate (1.8a)

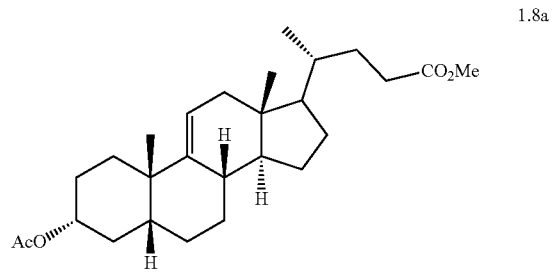

1.8a

To a solution of compound 1.7a (3 g, 7 mmol) in EtOAc (60 mL) was added 10% Pd/C (300 mg, 10% wt/wt), and the resulting slurry was hydrogenated in a Parr apparatus (70 psi) for 14-16 h. At this point the reaction was determined to be complete by TLC (10% ethyl acetate in hexanes). The mixture was filtered through a small plug of CELITE® (diatomaceous earth) and the solvent was removed under vacuum, affording compound 1.8a (2.6 g, 86%) as a white solid.

$^1$H NMR (500 MHz, CDCl$_3$): δ=5.31 (s, 1H), 4.73 (m, 1H), 3.66 (s, 3H), 2.37-2.03 (m, 7H), 2.01 (s, 3H), 1.98-1.09 (m, 18H), 1.06 (s, 3H), 0.92-0.91 (d, J=6.0 Hz, 3H), 0.59 (s, 3H).

ELSD Purity: 95.9%, ret. time=4.75, (Water symmetry shield 250×4.6 mm 5µ), ACN:Water (60:40)

Example 10

Methyl 3α-hydroxy-5β-chol-9(11)-en-12-one-24-oate (1.9a)

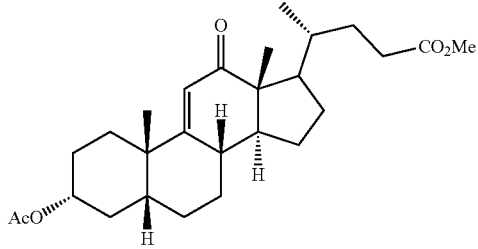

CrO$_3$ (17.0 g, 170 mmol) was added to a solution of compound 1.8a (17 g, 39.5 mmol) in AcOH (270 mL). The resulting mixture was heated at 50° C. for 24-36 h. Upon complete disappearance of the starting material by TLC, the solvent was evaporated under vacuum and the crude material was dissolved in ethyl acetate (400 mL) and water (200 mL). The two phases were separated and the organic layer was washed twice with water (2×100 mL) and then once with saturated brine solution (100 mL). The organic phase was dried over anhydrous Na$_2$SO$_4$ (40 g) and filtered. The filtrate was concentrated under vacuum and the resulting solid was purified by column chromatography [49 mm (W)×600 mm (L), 60-120 mesh silica, 120 g], eluting with ethyl acetate/hexane (1:5) [10 mL fractions, 3 mL/min elution, monitored by TLC and detected with UV light (254 nm) lamp]. The product-containing fractions were combined and concentrated under vacuum to afford compound 1.9a (8.8 g, 50% yield) as a white solid.

TLC: p-anisaldehyde charring, R$_f$ for 1.9a=0.28 and R$_f$ for 18a=0.52.

TLC mobile phase: 20%-EtOAc in hexanes.

$^1$H NMR (500 MHz, CDCl$_3$): δ=5.71 (s, 1H), 4.71-4.75 (m, 1H), 3.66 (s, 3H), 2.37-2.42 (m, 3H), 2.02-2.31 (m, 2H), 2.0 (s, 3H), 1.67-1.98 (m, 9H), 1.24-1.56 (m, 9H), 1.19 (s, 3H), 1.01-1.02 (d, J=6.5 Hz, 3H), 0.90 (s, 3H).

$^{13}$C NMR (500 MHz, CDCl$_3$): δ=204.9, 174.5, 170.4, 163.8, 123.6, 73.7, 53.4, 53.0, 51.3, 47.2, 41.7, 39.8, 37.7, 35.2, 35.0, 33.9, 31.4, 30.5, 29.6, 27.6, 27.3, 26.4, 26.1, 24.1, 21.2, 19.4, 10.6.

Mass (m/z)=445.0 [M$^+$+1], 462.0 [M$^+$+18].

IR=3437, 3045, 2946, 2870, 1729, 1680, 1252, 1168, 1020, cm$^{-1}$.

m.p.=137-139° C. (from EtOAc/hexanes mixture).

[α]$_D$=+93 (c=1% in CHCl$_3$).

ELSD Purity: 94.6%: Retention time=8.68 (Inertsil ODS 3V, 250×4.6 mm, 5 um, ACN:Water (60:40)

Example 11

Methyl 3α-acetoxy-5β-cholan-12-one-24-oate (2.0a)

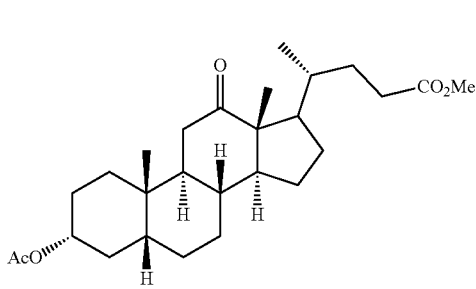

10% Pd/C (900 mg) was added to a solution of compound 1.9a (2.0 g, 4.5 mmol) in EtOAc (150 mL) and the resulting slurry was hydrogenated in a Parr apparatus (50 psi) at 50° C. for 16 h. At this point the reaction was determined to be complete by TLC. The mixture was filtered through a small plug of CELITE® (diatomaceous earth) and the solvent was removed under vacuum, providing compound 2.0a (1.6 g, 80% yield) as a white solid.

TLC: p-anisaldehyde charring, R$_f$ for 2.0=0.36 and R$_f$ for 1.9=0.32.

TLC mobile phase: 20%-EtOAc in hexanes.

$^1$H NMR (500 MHz, CDCl$_3$): δ=4.67-4.71 (m, 1H), 3.66 (s, 3H), 2.45-2.50 (t, J=15 Hz, 2H), 2.22-2.40 (m, 1H), 2.01 (s, 3H), 1.69-1.96 (m, 9H), 1.55 (s, 4H), 1.25-1.50 (m, 8H), 1.07-1.19 (m, 2H), 1.01 (s, 6H), 0.84-0.85 (d, J=7.0 Hz, 3H).

$^{13}$C NMR (125 MHz, CDCl$_3$): δ=214.4, 174.5, 170.4, 73.6, 58.5, 57.4, 51.3, 46.4, 43.9, 41.2, 38.0, 35.6, 35.5, 35.2, 34.8, 32.0, 31.2, 30.4, 27.4, 26.8, 26.2, 25.9, 24.2, 22.6, 21.2, 18.5, 11.6,

Mass (m/z)=447.0 [M$^+$+1], 464.0 [M$^+$+18].

IR (KBr)=3445, 2953, 2868, 1731, 1698, 1257, 1029 cm$^1$.

m.p.=142.2-144.4° C. (from EtOAc/hexanes mixture).

[α]$_D$=+92 (c=1% in CHCl$_3$).

ELSD Purity: 96.6%: Retention time=9.93 (Inertsil ODS 3V, 250×4.6 mm, 5 um, ACN: 0.1% TFA in water (90:10)

Example 12

Methyl 3α-acetoxy-12α-hydroxy-5β-cholan-24-oate (2.1a)

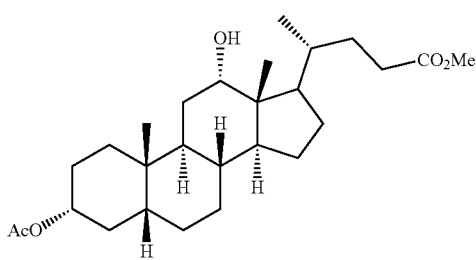

A THF solution of lithium tri-tert-butoxyaluminum hydride (1 M, 22.4 mL, 22.4 mmol) was added drop wise to a solution of compound 2.0a (2.5 g, 5.6 mmol) in THF (25 mL) at ambient temperature. After stirring for an additional 4-5 h, the reaction was determined to be complete by TLC. The reaction was quenched by adding aqueous HCl (1 M, 10 mL) and the mixture was diluted with EtOAc (30 mL). The phases were separated and the organic phase was washed sequentially with water (15 mL) and saturated brine solution (10 mL). The organic phase was then dried over anhydrous $Na_2SO_4$ (3 g) and filtered. The filtrate was concentrated under vacuum and the resulting solid was purified by column chromatography [29 mm (W)×500 mm (L), 60-120 mesh silica, 50 g], eluting with EtOAc/hexane (2:8) [5 mL fractions, monitored by TLC with p-anisaldehyde charring]. The fractions containing the product were combined and concentrated under vacuum to provide compound 2.1a (2.3 g, 91%) as a white solid.

TLC: p-anisaldehyde charring, $R_f$ for 2.1a=0.45 and $R_f$ for 2.0a=0.55.

TLC mobile phase: 30%-EtOAc in hexanes.

$^1$H NMR (500 MHz, $CDCl_3$): δ=4.68-4.73 (m, 1H), 3.98 (s, 1H), 3.66 (s, 3H), 2.34-2.40 (m, 1H), 2.21-2.26 (m, 1H), 2.01 (s, 3H), 1.75-1.89 (m, 6H), 1.39-1.68 (m, 16H), 1.00-1.38 (m, 3H), 0.96-0.97 (d, J=5.5 Hz, 3H), 0.93 (s, 3H), 0.68 (s, 3H).

$^{13}$C NMR (125 MHz, $CDCl_3$): δ=174.5, 170.5, 74.1, 72.9, 51.3, 48.1, 47.2, 46.4, 41.7, 35.8, 34.9, 34.7, 34.0, 33.5, 32.0, 30.9, 30.8, 28.6, 27.3, 26.8, 26.3, 25.9, 23.4, 22.9, 21.3, 17.2, 12.6

Mass (m/z)=449.0 [W+1], 466.0 [W+18].

IR (KBr)=3621, 2938, 2866, 1742, 1730, 1262, 1162, 1041, $cm^{-1}$.

m.p=104.2-107.7° C. (from EtOAc).

$[α]_D$=+56 (c=1% in $CHCl_3$).

ELSD Purity: 97.0%: Retention time=12.75 (Inertsil ODS 3V, 250×4.6 mm, 5 um, ACN:Water (60:40)

Example 13

Deoxycholic acid (DCA)

A solution of LiOH (187 mg, 4.4 mmol) in $H_2O$ (2.0 mL) was added to a solution of compound 2.1a (500 mg, 1.11 mmol) in THF (8 mL) and MeOH (8 mL). The resulting mixture was stirred for 3-4 h at 50° C. Upon complete disappearance of the starting material by TLC, the reaction mixture was concentrated under vacuum. A mixture of water (10 mL) and 3 N HCl (1 mL) were combined and cooled to 0° C. and then added to the crude product. After stirring for 1 h at 0° C., the precipitated solids were filtered and then washed with water (10 mL) and hexane (20 mL). Drying under vacuum at room temperature provided deoxycholic acid (DCA, 400 mg, 91% yield) as a white solid.

TLC: p-anisaldehyde charring, $R_f$ for DCA=0.32 and $R_f$ for 2.1a=0.82.

TLC mobile phase: 10%-Methanol in DCM.

$^1$H NMR (500 MHz, DMSO): δ=11.92 (s, 1H), 4.44 (s, 1H), 4.19 (s, 1H), 3.77 (s, 1H), 3.35-3.36 (m, 1H), 2.19-2.21 (m, 1H), 2.08-2.10 (m, 1H), 1.73-1.80 (m, 4H), 1.43-1.63 (m, 6H), 1.15-1.35 (m, 12H), 0.98-1.05 (m, 2H), 0.89-0.90 (d, J=6.0 Hz, 3H), 0.83 (s, 3H), 0.58 (s, 3H).

$^{13}$C NMR (125 MHz, DMSO): δ=174.8, 71.0, 69.9, 47.4, 46.1, 46.0, 41.6, 36.3, 35.6, 35.1, 34.9, 33.8, 32.9, 30.8, 30.7, 30.2, 28.6, 27.1, 27.0, 26.1, 23.5, 23.0, 16.9, 12.4.

Mass (m/z)=393 [M$^r$, +1].

IR=3363, 2933, 2863, 1694, 1453, 1372, 1042, $cm^{-1}$.

m.p.=171.4-173.6° C. (from ethanol); 174-176° C. (Alfa Aesar) and 171-174° C. (Aldrich)

$[α]_D$=+47 (c=1% in EtOH), +54° (c=2% in ethanol) [Alfa Aesar]

ELSD Purity: 99.7%: Retention time=5.25 (Inertsil ODS 3V, 250×4.6 mm, 5 um, ACN: 0.1% TFA in water (90:10).

Biological Example 1

Primary human adipocytes were incubated with varying concentrations of synthetic sodium deoxycholate synthesized using 9-HAD as starting material or bovine-derived sodium deoxycholate obtained from Sigma as described below.

Materials

Adipocytes (Zen-Bio cat #SA-1096)

96 well plates (US Scientific cat # cellstar no. 655180)

Serum-free RPMI medium (Mediatech cat #17-105-CV)

Sodium deoxycholate (DC) (Sigma cat #D6750)

Synthetic Sodium glycodeoxycholate (Kythera)

PBS (1×)

MTS assay kit (Promega cat #G3580)

Adipocytes arrived differentiated and at a density of 13,000 cells per well in a 96 well plate. Two plates were received and each treated with the same samples. Cells were incubated for 24 hours at 37° C. with 5% $CO_2$. A 1% stock solution of each bile acid (synthetic and non-synthetic DCA) were made by dissolving 20 mg into 2 mL media (serum-free). Using the 1% stock solution, the following 11 solutions were prepared by dilution: 0.005%, 0.01%, 0.015%, 0.02%, 0.025%, 0.03%, 0.035%, 0.04%, 0.05%, 0.06%, and 0.1%, as well as 0% (media only).

Cells were washed 2× with 150 μL of room temperature 1×PBS (phosphate buffered saline). Media and then PBS were removed from the wells in a 96 well plate by turning the plate upside down and decanting the liquid into a container. After the last PBS wash, 80 μL of sample was added per well. Each concentration of a specific bile acid was added to 8 wells and incubated for 1 hour at 37° C. with 5% $CO_2$. Plates were then removed from incubator and solution was decanted. A 100 μL solution of diluted (40 μL in 1 mL of RPMI) MTS reagent (3-(4,5-dimethylthiazol-2-yl)-5-(3-carboxymethoxyphenyl)-2-(4-sulfophenyl)-2H-tetrazolium, inner salt) was added directly to each well. Plates were incubated at 37° C. with 5% $CO_2$ until control (no bile acid) wells changed color to orange-brown and then loaded onto a spectrophotometer that analyzes 96 well plates. Samples were run at 490 nm wavelength setting.

Cell viability was assessed using a colorimetric assay (MTS) kit from Promega. The results show a dose-dependent decrease in cell survival upon treatment with either syn-NaDC or Sigma-NaDC (see FIG. 1). Both molecules demonstrated similar cytolytic behavior in this experiment, indicating that synthetic-NaDC and bovine-derived Sigma-NaDC are functionally identical in terms of their ability to kill fat cells.

The embodiments and example described above are not intended to limit the invention. It should be understood that numerous modifications and variations are possible in accordance with the principles of the present invention.

What is claimed is:

1. A method for preparing deoxycholic acid (DCA) or a pharmaceutically acceptable salt thereof:

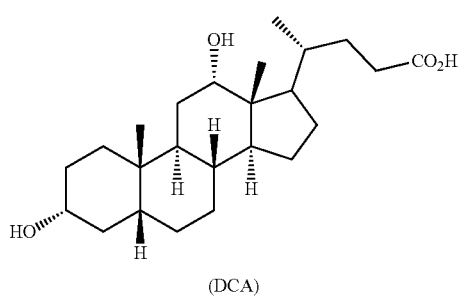

(DCA)

said method comprising:

(a) reacting a compound of formula 1.7 with $H_2$ under hydrogenation conditions to form a compound of formula 1.8 wherein P is a protecting group and R is alkyl

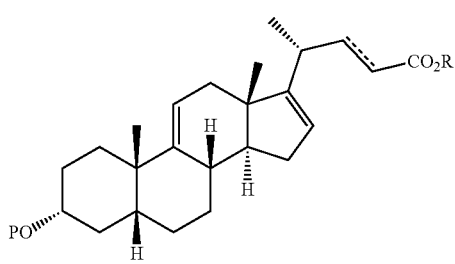

1.7

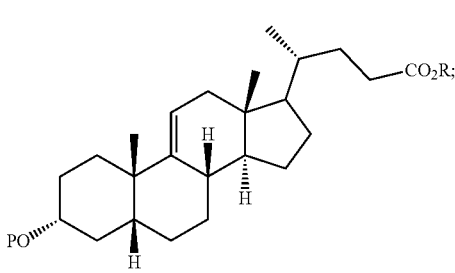

1.8

(b) reacting the compound of formula 1.8 with an oxidizing agent to form a compound of formula 1.9 wherein P is a protecting group and R is alkyl

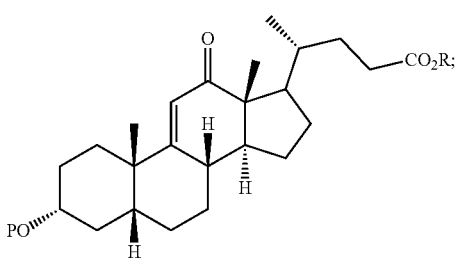

1.9

(c) reacting the compound of formula 1.9 with $H_2$ under hydrogenation conditions to form a compound of formula 2.0 wherein P is a protecting group and R is alkyl

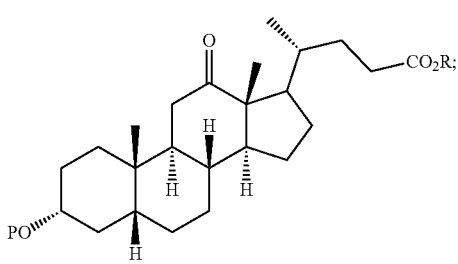

2.0

(d) reacting the compound of formula 2.0 with a reducing agent to form a compound of formula 2.1 wherein P is a protecting group and R is alkyl

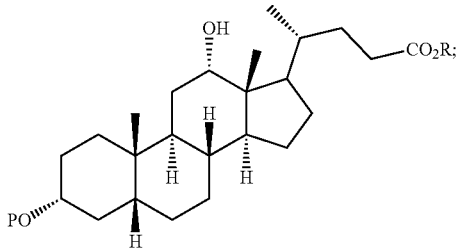

2.1 and (e) exposing the compound of formula 2.1 to deprotection and hydrolysis conditions to form deoxycholic acid.

2. The method of claim 1, wherein the hydrogenation conditions of part (a) comprise a $PtO_2$ catalyst.

3. The method of claim 1, wherein the oxidizing agent of part (b) is $CrO_3$.

4. The method of claim 1, wherein the hydrogenation conditions of part (c) comprise a Pd/C catalyst.

5. The method of claim 1, wherein the hydrogenation conditions of part (c) comprise a $PtO_2$ catalyst.

6. The method of claim 1, wherein the reducing agent of part (d) is $LiAl(OtBu)_3H$.

7. The method of claim 1, wherein P is —C(O)CH$_3$.

8. The method of claim 7, wherein the deprotection and hydrolysis conditions of part (e) comprise reacting compound 2.1 with an alkali earth alkoxide, an alkali metal hydroxide, or a mixture of both.

9. The method of claim 7, wherein the deprotection and hydrolysis conditions of part (e) comprise reacting compound 2.1 with LiOH.

10. The method of claim 1, wherein R is CH$_3$.

* * * * *